United States Patent
Gjerde et al.

(10) Patent No.: US 12,037,633 B2
(45) Date of Patent: Jul. 16, 2024

(54) METHODS, DEVICES AND KITS FOR PREPARING NUCLEIC ACID SAMPLES FOR STORAGE AND ANALYSIS

(71) Applicant: VosBio, Inc., San Jose, CA (US)

(72) Inventors: Douglas T. Gjerde, Saratoga, CA (US); David Peter Joseph Hornby, Widnes (GB)

(73) Assignee: VOSBIO, INC., San Jose, CA (US)

( * ) Notice: Subject to any disclaimer, the term of this patent is extended or adjusted under 35 U.S.C. 154(b) by 348 days.

(21) Appl. No.: 17/231,234

(22) Filed: Apr. 15, 2021

(65) Prior Publication Data

US 2021/0355525 A1    Nov. 18, 2021

Related U.S. Application Data

(60) Provisional application No. 63/164,520, filed on Mar. 22, 2021, provisional application No. 63/163,032, filed on Mar. 18, 2021, provisional application No. 63/124,048, filed on Dec. 10, 2020, provisional application No. 63/073,447, filed on Sep. 1, 2020, provisional application No. 63/052,269, filed on Jul. 15, 2020, provisional application No. 63/049,626, filed on Jul. 8, 2020, provisional application No. 63/042,552, filed on Jun. 22, 2020, provisional application No. 63/010,455, filed on Apr. 15, 2020.

(51) Int. Cl.
*C12Q 1/6806* (2018.01)
*A61B 10/00* (2006.01)
*C12N 15/10* (2006.01)

(52) U.S. Cl.
CPC ........ *C12Q 1/6806* (2013.01); *A61B 10/0051* (2013.01); *C12N 15/1003* (2013.01)

(58) Field of Classification Search
None
See application file for complete search history.

(56) References Cited

U.S. PATENT DOCUMENTS

| | | | |
|---|---|---|---|
| 7,118,537 B2 | 10/2006 | Baddour | |
| 2004/0157218 A1* | 8/2004 | Collis | C12Q 1/6806 435/270 |
| 2009/0233309 A1* | 9/2009 | Fischer | C12N 15/1003 435/6.1 |
| 2016/0108463 A1 | 4/2016 | Fischer et al. | |
| 2017/0051333 A1 | 2/2017 | Warnken | |
| 2017/0073738 A1* | 3/2017 | Fischer | C12Q 1/701 |

FOREIGN PATENT DOCUMENTS

| | | | |
|---|---|---|---|
| WO | WO-2006138444 A2 * | 12/2006 | ............ C12N 1/06 |
| WO | WO 2016/037099 A1 | 3/2016 | |
| WO | WO 2018/126119 A1 | 7/2018 | |
| WO | WO 2018/198682 A1 | 11/2018 | |

OTHER PUBLICATIONS

Leung, N.H.L. et al., Respiratory virus shedding in exhaled breath and efficacy of face masks, Nature Medicine, vol. 26, pp. 676-680, plus methods (one page), plus extended data pp. 1-11 (Year: 2020).*
Rais et al., Method to screen substrates of apical sodium-dependent bile acid transporter. AAPS J. Dec. 2008;10(4):596-605. doi: 10.1208/s12248-008-9069-9. Epub Dec. 16, 2008. PMID: 19085111; PMCID: PMC2628203 (Year: 2008).*
International Search Report and Written Opinion for International Patent Application No. PCT/EP2021/059815, 19 pages, Sep. 24, 2021.
Combined Search and Examination Report under Sections 17 and 18(3), App. No. GB2105390.5, Sep. 22, 2021.
Ahmadzai et al., "Exhaled breath condensate: a comprehensive update", Clin Chem Lab Med, Feb. 2013, 51(7): 1343-1361. DOI 10.1515/cclm-2012-0593.

* cited by examiner

*Primary Examiner* — Aaron A Priest
*Assistant Examiner* — Tian Yu
(74) *Attorney, Agent, or Firm* — ORRICK, HERRINGTON & SUTCLIFFE LLP

(57) ABSTRACT

Methods, devices and kits for sampling, releasing and stabilizing nucleic acid, including RNA and DNA, from virus, bacteria yeast and other cells is described. The released and stabilized nucleic acid may be analyzed and quantified without further sample preparation at the point of care or may be transported to a testing laboratory by shipment and analyzed directly. The nucleic acid, which can be RNA, remains safe and stable so that shipping by normal means including government postal service may be used. In addition, the RNA sample remains stable so that analysis can be performed immediately after receipt of sample or after storage for days, weeks or months. Storage may be at room or ambient temperature or cooler temperatures. The sampling apparatus used to acquire samples can interface with nucleic detection and measurement instrumentation including high throughput, parallel processing instruments.

20 Claims, 9 Drawing Sheets

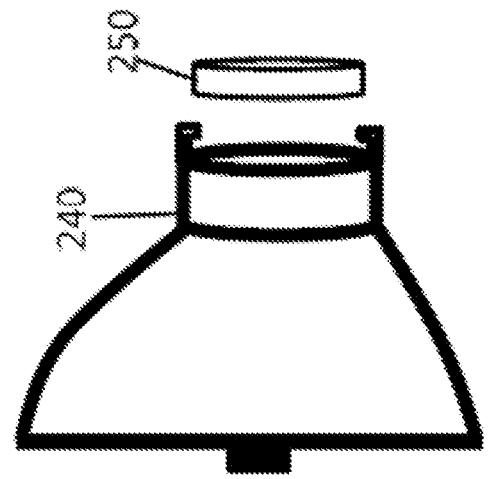
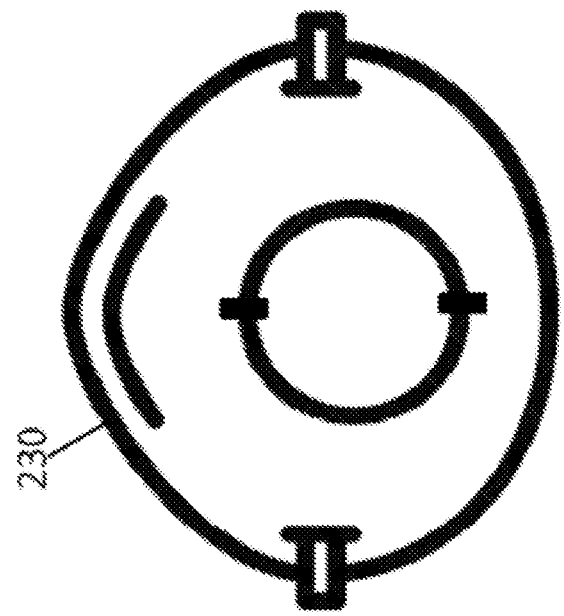
Figure 6B
Figure 6A

METHODS, DEVICES AND KITS FOR PREPARING NUCLEIC ACID SAMPLES FOR STORAGE AND ANALYSIS

REFERENCE TO PRIOR APPLICATIONS

This application claims priority to U.S. Provisional Application Nos. 63/010,455 filed on Apr. 15, 2020, 63/042,552 filed on Jun. 22, 2020, 63/049,626 filed on Jul. 8, 2020, 63/052,269 filed on Jul. 15, 2020, 63/073,447 filed on Sep. 1, 2020, 63/124,048 filed on Dec. 10, 2020, 63/163,032 filed on Mar. 18, 2021, and 63/164,520 filed on Mar. 22, 2021, all of which are incorporated herein by reference.

FIELD OF THE INVENTION

The present invention relates to methods, devices and kits for preparing nucleic acid for analysis from biological samples that allows the nucleic acid to be stabilized allowing storage, and in particular nucleic acid samples comprising viral RNA and viral DNA and analysis for viral nucleic acid antigens.

BACKGROUND OF THE INVENTION

Viruses replicate only in living cells. Viruses cause disease by destroying or damaging the cells they infect, damaging the body's immune system or causing inflammation that can damage an organ. Viruses cause many types of diseases, such as COVID-19 (caused by Severe Acute Respiratory Syndrome Corona Virus-2, SARS-CoV-2), Acquired Immune Deficiency Syndrome (AIDS, caused by Human Immuno-deficiency Virus, HIV), cold sores, chickenpox, measles, flu, influenza, some types of cancer and others. Other examples include Herpes simplex, varicella-zoster virus (VZV), Respiratory syncytial virus (RSV), Epstein-Barr virus, Cytomegalovirus (CMV), Coronaviruses, Rotavirus, Hepatitis, Genital warts (human papillomavirus, or HPV), Influenza (flu), and BK virus.

Viruses vary in their structure. A virus particle consists of nucleic acids within a protective protein coat called a capsid. The shape of the capsid may vary from one type of virus to another. The capsid is made from proteins encoded by viral genes. Some viruses have an outer protein envelope that can have lipids associated or embedded. The outer envelope layer may contain protein spikes or protrusions. Most viruses have either RNA or DNA as their genetic material. The nucleic acid may be single- or double-stranded. The simplest viruses contain only enough RNA or DNA to encode four proteins. COVID-19 has 29 outer proteins.

The detection of present or past virus can be performed by looking for the product of a virus infection. Antibodies are produced by the body's immune system in response to invasion by a foreign antigen such as a virus or bacterium. A positive test for antibodies raised against these antigens indicates the presence of the disease in a person recently infected or infected some time ago. Typically, a blood sample is needed for this testing which must be taken by qualified personnel.

A sample-containing virus may also contain human cells or other biomaterials. In classical virus diagnostic methods, RNases other enzymes and human cellular components are removed and the viral nucleic acid is captured using a nucleic extraction column or magnetic beads. Chemical reagents such as chaotropic reagents or other reagents are added to the sample mixture to give the column/magnetic beads strong selectivity for the viral nucleic acid.

In some cases, this viral nucleic acid purification process is based on silica membranes or chaotropic silica purification media methodology. In some cases, the nucleic acid purification is based on ion exchange. RNA or other nucleic acids may be detected and quantified to measure the presence and quantity of virus in a biological sample. Then, the purified RNA or DNA is amplified and detected using an amplification process.

Testing for an active viral infection can be performed by measuring one or more viral antigens. The interaction between a viral antigen and test antibody is often amplified and detected using either a secondary antibody which is tagged with either an enzyme (in the case of ELISA) or a fluorescent molecule (a dye or a tracer). Specially tagged antibodies that attach to those viral antigens are mixed with the sample, usually a blood sample. If the tagged antibodies recognize and bind to the target antigen, the individual is infected with the virus. A viral antigen detection test is done on a blood sample, or a biopsy of tissue that might be infected, again requiring skilled personnel to implement the test and evaluate the outcome. The viral antigen test may be performed from throat swabs, saliva etc. In these cases, the antigen may no longer be associated with the viral RNA. Thus, antigen tests are inexpensive and rapid, but the results are unreliable for determining an active viral infection.

Direct testing of the viral nucleic acid is needed to obtain accurate results. A direct viral nucleic acid detection test can be used to determine the presence, the amount and the specific nucleotide sequences of the genetic material (DNA or RNA) of a specific virus. The detection technology used can be a nucleic acid amplification technology (NAAT). This test can show the particular virus causing an infection. The test can also show if a virus is present at the time of testing. Therefore, this test is useful or even necessary to prescribe immediate treatment to a patient manifesting symptoms of the disease.

Different types of samples are used for a viral test, including blood, urine, stool (feces), organ tissue, spinal fluid, nasal material, sputum and saliva. In one method of sampling, the test starts with taking a swab from the nose or the back of the throat, and then carefully inserting the swab into a sterile tube. The sample is stored until analysis. Then the sample is mixed with a chemical solution that breaks open the virus and releases its nucleic acid genome (DNA or RNA). The nucleic acid is extracted by a column filled with media or magnetic beads and recovered. The recovered nucleic acid is subsequently mixed with the appropriate reagents and inserted into a qPCR instrument, LAMP instrument or similar nucleic acid detection instrument. The instrument specifically amplifies the viral nucleic acid allowing detection of select sequences of the viral genome and ignores contamination from other nucleic acids, which may derive from the environment, host-cell-specific tissue, operator contamination or from other viruses and microbes.

While some sampling such as from blood and spinal fluid must be performed by skilled personnel, in theory, sampling from urine, feces, sputum could be performed at home. However, the virus produced by these sampling methods is unstable and skilled personnel are still necessary for reliable and accurate results. In addition, unless analysis is performed at the point-of-care, sampling and transporting the sample to an instrument at a separate location requires special tools and procedures. The virus remains active and contagious in these samples and must be handled in a manner that prevents exposure to humans of the live virus.

Guidance for COVID-19 testing was provided by the WHO in their Interim Guidance released Mar. 19, 2020, "Laboratory testing for coronavirus disease (COVID-19) in suspected human cases." In the document, the specimen type, collection materials and storage temperature until testing in a laboratory, and the recommended temperature for shipment according to expected shipment time are listed. The guidelines state that specimens for virus detection should reach the laboratory as soon as possible after collection. Correct handling of specimens during transportation is essential. Specimens that can be delivered promptly to the laboratory can be stored and shipped under refrigerated conditions at 2-8° C. When there is likely to be a delay in specimens reaching the laboratory, the use of viral transport medium is strongly recommended. Viral transport medium (VTM) contains only antifungal and antibiotic supplements along with a range of stabilizing components. Specimens may be frozen to −20° C. or ideally −70° C. and shipped on dry ice if further delays are expected. It is important to avoid repeated freezing and thawing of specimens.

The WHO document further specifies the transport of specimens within national borders should comply with applicable national regulations. International transport of samples that potentially contain COVID-19 virus should follow the UN Model Regulations, and any other applicable regulations depending on the mode of transport being used. More information may be found in the WHO Guidance on regulations for the Transport of Infectious Substances 2019-2020 and WHO interim guidance. All sample collection must be compliant with the latest international World Health Organization protocols and the national protocols including the Public Health England in the United Kingdom and the Centers for Disease Control in the USA. These guidelines are also stated in WHO document: "Packaging and shipment of clinical specimens".

While direct viral nucleic acid detection is selective, sensitive and indicates the presence or absence of an active infection, sampling and transport followed by analysis of the sample is not rugged or robust and must be done under carefully controlled conditions. Moreover, RNA is intrinsically unstable, and the analysis must be done quickly after sampling. In particular, for example, ribonuclease enzymes (RNases) or present in the sample will quickly destroy the RNA. The samples are extracted at the laboratory with the addition of reagents and an extraction column or mag beads to purify and recover the nucleic acid from other contaminants including RNase.

Samples are fragile and for current sampling methods, samples cannot be easily delivered through the government postal service because delivery times may take two, three or more days. It may be difficult under current technology to perform remote sampling of viruses containing RNA. Sampling may not be reliable under any circumstances with even a short delay from sampling and analysis. For example, group sampling (sampling of in individuals in a particular defined group) may produce unreliable results because of the time elapsed between the first and the last sample taken within the group. In addition, viral samples can be dangerous and must be handled carefully under controlled procedures.

It therefore remains a problem in this area to provide a rapid and easy to use method for the preparation and stabilization of nucleic acid samples prior to diagnostic testing, in particular one that permits the safe storage and transport of samples, while ameliorating degradation of nucleic acids in the sample and/or one that simplifies preparing the sample for detection.

SUMMARY OF THE INVENTION

Broadly, the present invention provides methods, devices and kits that enable the sampling, release and preservation of the nucleic acid from virus, bacteria, yeast, tissue cells or other cells. In particular, the present invention provides a group of solvents that can be used, alone or in combination to release the nucleic acid and preserve the nucleic acid. The released and preserved nucleic acid may be analyzed directly without further sample preparation or purification. The devices and method of the invention are suitable for any nucleic acids, particularly RNA.

The released and stabilized nucleic acid may be identified and quantified at the point of care where the sample is taken. Or, the nucleic acid sample may be mailed, shipped or transported to a testing laboratory where the analysis is performed. In some embodiments of the invention, the device and method of the invention may be used for viral RNA. The method and device of the invention provides RNA that is stable at room and ambient temperatures.

In some embodiments, RNA in the sample remains stable so that shipping by normal means including government postal service may be used. In addition, the RNA sample remains stable so that analysis can be performed at will after receipt of sample at the laboratory.

Detection may be performed directly on the sample without the need to first capture the nucleic acid using an extraction column or magnetic beads. Nucleic acid detection and quantification may be performed by different technologies including PCR, qPCR, LAMP, EXPAR or similar nucleic acid amplification and detection methods. Alternatively, nucleic acids can be identified without amplification for example, using single molecule sequencing. RNA molecules can also be detected and manipulated through amplification via the use of reverse transcriptases (RT), which are RNA-dependent DNA Polymerases. RTs polymerize a strand of DNA that is complimentary to the original RNA template and is referred to as cDNA. This cDNA can then be further amplified through PCR, qPCR or isothermal methods as outlined above or detected in a single reaction using one-step RT-qPCR or RT-LAMP. In some methods, detection can be direct. In other methods detection may be performed using mass spectrometry, sequencing, etc. The detection technology can be NAAT, nucleic acid amplification technology.

The solvents of the present invention have several different properties and performs several different operations. First, the solvents are water-miscible organic solvents that are able to combine with the sample. Second, the solvents are lipid or cell wall solubilizing or disrupting to release the nucleic acid. Third, the solvents denature or disable proteins, specifically DNase and RNase, to prevent the nucleic acid from being degraded by enzymes. Fourth, the solvents of the present invention are capsid or protein disrupting which releases the nucleic acid into solution. Frequently, nucleic acids are associated with proteins in virus, bacteria and other cells. The solvents of the present invention promote release of the nucleic acid while still performing function three, denaturing or disabling of proteins. Fifth, the solvents do not prevent the amplification of the nucleic acid. This is surprising given the nature of the solvents to disable or denature proteins. Amplification of RNA is dependent on the action of reverse transcriptase, an enzyme that produces cDNA (complimentary DNA) as a first step in amplification. Next, the cDNA can be amplified through a DNA amplification process. The DNA amplification is dependent on a polymerase for thermal cycling or loop amplification. Proteins of some type are required to amplify the nucleic acids so it is surprising that amplification can be accomplished in the presence of the solvents that disable or denature DNase and RNase. Finally, sixth, the solvents of the present invention do not precipitate the nucleic acid as at least a fraction of soluble nucleic acid is needed for amplification and detection. As nucleic acids are ionic and hydrophilic and water molecules stabilize the structure, some organic solvents, such as ethanol and isopropyl alcohol, displace water from the structure and precipitate nucleic acids and more generally organic solvent precipitation is a common method for precipitation, concentration and purification of nucleic acids. In contrast, the solvents of the present invention are organic and water-miscible, but do not precipitate nucleic acids. In some embodiments of the invention, acetonitrile is the solvent. Acetonitrile can be combined with biological samples to prepare, release and stabilize nucleic acid for amplification, detection and quantification. In some embodiments of the invention acetonitrile disrupts the lipid and capsid of a virus releasing the RNA. The solvent disables the RNase to prevent degradation of the sample. The sample is optionally diluted and then added to a master mix which contains all the reagents needed for RT-PCR, qPCR or other amplification and detection methods. Optionally, the solvent of the invention is in the master mix. The process of lysing the cell and stabilizing the sample can be performed in the amplification tube. Acetonitrile or another solvent of the invention can be added in sufficient concentration to release the RNA and disable RNase.

A variety of solvents are suitable for use in accordance with the present invention. Water-miscible solvents that are suitable for release and stabilization of viral RNA include acetonitrile, tetrahydrofuran (THF), N,N-dimethylformamide (DMF), acetone and dimethyl sulfoxide (DMSO), and other aprotic, water-miscible solvents. Aprotic solvents that only are partially water-miscible such as ethyl acetate also work for this invention. Preferably, the methods, devices and kits of the present invention employ acetonitrile, acetone and DMSO as these solvents perform well in the context of the present invention. Acetone and DMSO have low toxicity and can be shipped easily. In some embodiments of the invention, a protic solvent is used. In some embodiments of the invention, the solvent may contain a surfactant to enhance lysis and/or an ion pairing reagent and/or a pH adjusting buffer to enhance nucleic acid solubility.

In the methods, devices and kits of the present invention, sufficient solvent or reagent is added at the point of sampling or after sampling to provide ambient temperature, long-term nucleic acid stabilization. At the point of amplification, the solvent mixture containing the nucleic acid may be diluted prior to amplification. However, dilution may reduce sensitivity and only the minimum dilution is performed.

The solvent of the invention may be a single solvent or mixture of solvents including water-miscible organic solvents with additives.

Accordingly, in a first aspect, the present invention provides a method of preparing a biological sample prior to analysis, the method comprises:
  combining the biological sample and a water-miscible organic solvent in a sample container, wherein the water-miscible organic solvent (i) lyses virus or cells present in the biological sample to release nucleic acids into solution in the water-miscible organic solvent and (ii) denatures or deactivates RNase or DNase enzymes in the biological sample to reduce degradation of the nucleic acids, thereby providing a processed biological sample.

In a further aspect, the present invention provides a method of detecting a target nucleic acid in a processed biological sample, the method comprising:

(a) providing a processed biological sample according to the method as described herein;
(b) combining the processed biological sample with nucleic acid amplification reagents to amplifying the target nucleic acid in the presence of the water-miscible organic solvent to provide an amplified sample; and
(c) analyzing the amplified sample to detect the presence of the target nucleic acid.

In a further aspect, the present invention provides a method of detecting a target nucleic acid in a biological sample, the method comprises:

(a) combining the biological sample and a water-miscible organic solvent in a sample container, wherein the water-miscible organic solvent (i) lyses virus or cells present in the biological sample to release nucleic acids into solution in the water-miscible organic solvent and (ii) denatures or deactivates RNase or DNase enzymes in the biological sample to reduce degradation of the nucleic acids, thereby providing a processed biological sample;
(b) combining the processed biological sample with nucleic acid amplification reagents to amplifying the target nucleic acid in the presence of the water-miscible organic solvent to provide an amplified sample; and
(c) analyzing the amplified sample to detect the presence of the target nucleic acid.

In this aspect of the present invention, steps (a) and (b) may take place at the same time (i.e. simultaneously), for example by combining the biological sample with a composition that comprises the water-miscible organic solvent and the amplification reagents. Alternatively, the method also encompasses the situation in which the amplification reagents are added sequentially to the combined biological sample and amplification reagents, but prior to the solvent having a lysed the virus or cells and acted denature the RNase or DNase enzymes.

In a further aspect, the present invention provides a method of capturing, preparing and storing a biological sample present in the breath of a subject by breathing into a sample container, wherein the method comprises:
  providing the biological sample in a sample container by having a subject breathe into the sample container; and
  combining the biological sample with a water-miscible organic solvent,
  wherein the water-miscible organic solvent (i) lyses virus or cells present in the biological sample to release nucleic acids into solution in the water-miscible organic solvent and (ii) denatures or deactivates RNase or DNase enzymes in the biological sample to reduce degradation of the nucleic acids, thereby providing a processed biological sample.

In a further aspect, the present invention provides a kit for carrying out the method of any one of the preceding claims comprising a sample container for receiving the biological sample, a volume of a water-miscible organic solvent for combining the biological sample, wherein the water-miscible organic solvent (i) lyses virus or cells present in the biological sample to release nucleic acids into solution in the water-miscible organic solvent and (ii) denatures or deactivates RNase or DNase enzymes in the biological sample to reduce degradation of the nucleic acids, thereby providing a processed biological sample.

Optionally, the kit further comprises one or more of a buffer for mixing with the biological sample, a cap for the sample container, nucleic acid amplification reagents to amplifying the target nucleic acid (e.g. a viral antigen) in the presence of the water-miscible organic solvent, reagents for detecting the target nucleic acid and/or a mail-in packaging for sending a collected and processed biological sample to a laboratory for testing, depending on the context in which the kit is intended to be used.

In a further aspect, the present invention provides a device for collecting a biological sample from a subject's breath, the device comprising an inlet and an outlet for breath, a collection chamber and a cartridge containing a volume of a water-miscible organic solvent in communication with the chamber, wherein the subject breathing into the inlet causes exhaled breath particle to collect in a chamber and to pass into the cartridge where the biological sample collects in the water-miscible solvent which (i) lyses virus or cells present in the biological sample to release nucleic acids into solution in the water-miscible organic solvent and (ii) denatures or deactivates RNase or DNase enzymes in the biological sample to reduce degradation of the nucleic acids, thereby providing a processed biological sample.

The following is a description of the method steps of the invention including optional steps:

1. Acquire a sample from the biological source. Provide a sample containing yeast, bacteria, tissue cells, other cells, virus, etc. Biological sources of samples include in all organs, kidney, liver, lungs, nostril, saliva, mouth, cheek, feces, urine, blood, body liquids and excrements. The sample may be breath containing particles of virus or bacteria.
2. Contact sample with a polar, water-miscible, solvent reagent to release the viral nucleic acid. Mix the sample and solvent. The virus is not infectious and safe to handle after this step. Optionally, the solvent contains additives to promote the nucleic acid release and stabilization. Optionally, the solvent contains hydrogen peroxide or other oxidizing or reducing reagents. Optionally, the solvent contains a protein digestion enzyme. Optionally, the additives are added first to the sample and followed by the solvent.
3. Optionally, heat the sample solvent mixture, for example to improve lysis of the cells or viral particles to enhance the release of nucleic acids.
4. Optionally, place the stabilized nucleic sample into a shipping container such as a tube, vial, syringe, plate or other container that can be used for analysis. At this point, the present invention permits the optional storage of the sample.
5. Optionally, filter, centrifuge or separate solids from the liquid. Optionally, store sample.
6. Transport the sample to an instrument for analysis. Optionally, dilute the sample. optionally dilute.
7. Add amplification reagents—dilution may be performed as part of adding amplification reagents. Optionally, heat the reagent mixture containing the solvent and additives before amplification of the nucleic acid. Optionally, solvent of the invention may be added in this step with the amplification reagents.
8. Optionally, add positive and negative controls.
9. Amplify and detect the nucleic acid(s) of interest if present in the sample.

All steps of the process must be performed with reagents and processes that are compatible with the subsequent step. For examples, it is preferred that reagents added or processes performed do not prevent the reverse transcriptase, polymerase or other amplification or detection reagents from performing their function.

In some embodiments, sample collection may be performed at home and the sample transported to the analytical instrument. In some embodiments, the sampling may be performed at a school, airport, company or other place where a group of people gather or travel together.

Sterile transport containers can be used in accordance with the present invention but are not necessary. Sufficient of the solvent(s) of the invention can be used to prevent bacterial growth and otherwise protect the nucleic acid from degradation.

Although refrigeration can be used, for example at standard refrigeration temperatures between about 2° C. and about 8° C., the stabilized nucleic acid can also be stored at room temperature or ambient temperature, typically between about 15° C. and about 30° C.

Overnight shipping can be used however, slower shipping methods may also be used.

Immediate amplification and analysis can be performed or, amplification can be performed later. Amplification can be performed up to a day, week, month, 2 months, 3 months, 6 months, 9 months, 12 months, or indefinitely, after sampling and addition of the solvent(s) of the present invention.

In the sampling process and use of an associated device, the sample is stable. The virus is not infectious and RNases or DNases are inactivated.

The methods, devices and kits may be used to interface manual sampling with high throughput, parallel sample processing. The samples may be amplified one at a time or in parallel with other samples.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

All of the references mentioned herein are expressly incorporated by reference in their entirety.

The present invention will now be described by way of examples and not limitation with reference to the accompanying examples and figures.

BRIEF DESCRIPTION OF THE DRAWINGS

FIGS. 6A and 6B show a mask comprised of a filter for collection of virus, bacteria and chemicals.

FIG. 7A shows placement of the filter in a syringe. FIG. 7B shows addition of solvent and FIG. 7C shows aspiration of solvent into the syringe through a needle.

DEFINITIONS

Figure 1:
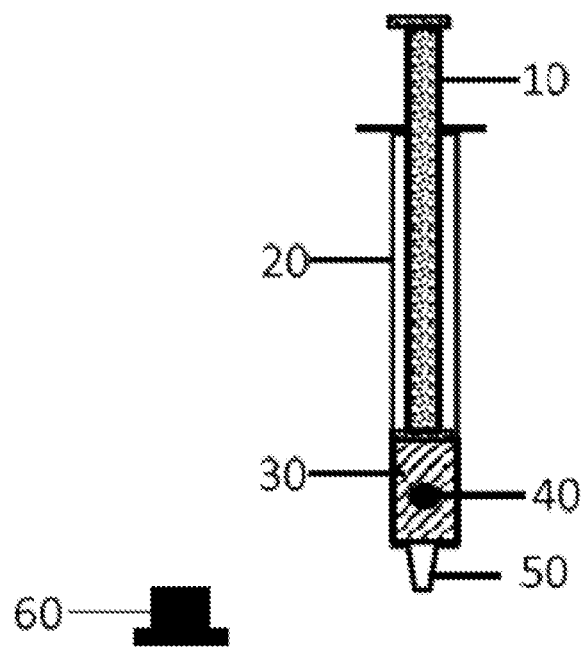
FIG. 1 is a syringe containing lysis and stabilization solvent with a mixing bead.

Sample: a biological sample containing nucleic acid for detection.

Processed biological sample: the biological sample treated with the water-miscible organic solvent of the present invention to lyse the virus or cells to release at least a proportion of the nucleic acids into solution in the solvent, and optionally then further treated by (a) adding a preservation buffer or other reagents for storage and/or (b) adding nucleic acid amplification reagents for amplifying a target nucleic acid in the sample.

Amplified sample: a processed biological sample which has undergone an amplification reaction to amplify the target nucleic acid, if present in the original biological sample.

Detection enzyme: protein enzyme used for transcribing or amplification of nucleic acid to detect nucleic acid.

Solvent: water-miscible organic solvent with optional additives that release nucleic acids from a cell or virus and stabilize nucleic acid. As used herein, references to using a "solvent" of the present invention includes the use of combinations of the solvents. In some cases, the water-miscible organic solvent may be substituted, all or in part, by hydrogen peroxide.

Ribostay: a formulation with solvent of the present invention.

Collection media: particles or material that collect biological materials from breath.

Collection surface: a surface designed to collect to collect biological material from breath. The surface can be sampled to detect the biological material.

Precipitate is defined herein as any solid derived from precipitation or other methods.

DETAILED DESCRIPTION OF THE INVENTION

Overview of the Present Invention

In current certified methods for nucleic acid amplification technique (NAAT), the virus sample is taken, and the virus preserved, as best as possible, before the analysis is performed. Then, when ready to perform the analysis, the virus-containing sample is treated with a surfactant, base, chaotrope and other reagents to release the nucleic acid. Then the sample is purified by a column or magnetic bead process to extract and recover the nucleic acid for analysis. Once released, purified and recovered, the nucleic acid is immediately amplified or detected using real time PCR, also called qPCR, LAMP, EXPAR or other amplification and detection enzymes and detection technologies. The amplified nucleic is detected and may be quantified.

The present invention provides methods, devices and kits for preparing cells for nucleic acid detection. A biological sample containing cells is acquired and a solvent reagent is added to release the nucleic acid from the cell structure. The solvent reagent also disables or deactivates DNase or RNase that may be present in the sample. The sample may be treated with solvent of the present invention at the time of sampling or later. The released and stabilized nucleic acid may be identified and quantified immediately at the point of source. The sample may also be brought to an instrument or shipped to a central laboratory to perform the analysis necessary to detect and quantify the virus. The process may be used for any cell biological material. RNA and/or DNA from the sample remains stable. Shipping may be accomplished safely with the virus disabled or "killed" and may be performed at ambient temperatures. The solvent process may also be used to release DNA from these materials and stabilize the DNA by disabling or denaturing DNase.

The solvents and processes used in accordance with the present invention represent a balance between being able to carry out four processes performed in the invention: 1) lysing the cell or virus to release of nucleic acid, 2) preservation of the nucleic acid by disabling of RNase and DNase by solvent of the invention, 3) for RNA nucleic acid reverse transcribing (if RNA) in the presence of solvent of the invention and 4) amplification and detection in the presence of the solvent of the invention. Therefore, each particular solvent that is used for the invention is optimized for each task while not preventing the next task. The impact of the use a solvent may also be improved to fulfil these criteria by the selection of suitable pHs and co-solvent molecules, including simple salts.

The general procedure involves combining a solvent with the sample, mixing, and either analyzing or storing. Storage may be short term i.e., only a few minutes, or longer term, an hour or several hours or even days or weeks. With proper storage, the solvent should not evaporate in the storage sample. The space above the solvent may be kept to a minimum to control and minimize evaporation. In some embodiments of the present invention the sample is analyzed directly from storage. In some embodiments, the solvent is removed before analysis with evaporation using heat, gas or speed evaporation (with vacuum) or a combination. In some embodiments of the present invention, water or buffer is added to the sample to dilute the solvent before analysis. The solvent preserves the sample until analysis. However, to amplify the nucleic acid, it might be necessary to dilute the solvent to re-activate the polymerase or other amplification reagents. The addition of solvent or buffer is preferred to be done with a sample preparation fixture or apparatus so that each sample is treated the same way for every sample. In some embodiments of the present invention, the stabilized sample is filtered or centrifuged before storage. In some embodiments of the present invention, the sample is filtered centrifuged before analysis. In some embodiments of the present invention, sample is added to the solvent in the detection mixture.

For sampling that is self-administered or performed by untrained personnel, the sampling device needs to be foolproof and socially acceptable. In some embodiments of the present invention, the sampling is a passive process, i.e., passive drool, urine, etc. In other embodiments of the invention, the sampling is an active process, i.e., swabbing, scraping, etc. Virus can be sampled from any part of the body including all organs, kidney, liver, lungs, nostril, mouth, cheek, feces, urine, blood, breath, saliva, body fluids and breath.

In some embodiments, the sample is obtained by breathing. In these embodiments, breath can be collected in any way e.g., breathing onto a surface or into a device or blowing through a straw or device that deposits the breath onto a surface. Alternatively, the breath can be bubbled through the solvent. A breath sample can be collected from a single breath, or breathing for a prolonged period for example, into a wearable device.

A sorbent pad or material can be used to collect the sample from the mouth or nose. After sampling, the biological sample can be deposited or squeezed out into a container. The container may contain the solvent of the present invention. Alternatively, the container may be taken up into a device or syringe containing solvent of the present invention. Alternatively, the sample may be taken up with a pipette or syringe and transferred to a vial which could contain the solvent of the invention. The sample may be taken by breathing or bubbling breath through the solvent of the invention. In some embodiments of the invention, a (one-way) check valve may be incorporated into a mouthpiece or blowing straw to ensure that breath and droplets are added to the solvent only in one direction. In this embodiment, solvent cannot be drawn back up straw into the mouth. In some embodiments of the present invention, breath droplets are deposited on a surface and the breath is collected and treated with a solvent.

The interface between manual sampling and automated sample preparation can be performed at any point in the process. After the sample is acquired, the sample may be placed in an instrument to extract and stabilize the sample with the solvent of the present invention. Alternatively, the sample may be stabilized and then the sample preparation step may be automated.

The methods may be used to stabilize RNA or DNA for samples of bacteria, yeast, fungi, etc. to prepare the sample for nucleic amplification and detection. For example, for bacteria, the sample may be preserved by releasing DNA (or RNA) and deactivation of DNase (or RNase). Contaminating bacteria can be killed by the solvent. Other material may be disabled by the solvent. Other biological samples may be stabilized in the solvent of the invention. Alternatively or additionally, the methods allows the direct amplification of nucleic acid without prior purification using a column or magnetic beads. However, the solvents of the present invention can also be used to lyse, preserve and stabilize RNA and DNA prior to purification by a column or magnetic beads and recovery of the nucleic acids. The nucleic acids that can be processed according to the present invention include modified forms of RNA (e.g. to accommodate modifications that accommodate biological activity such as replication or transcription) or DNA (e.g. include methylation, hydroxymethylation, glucosylation, etc.).

The Virus Diagnostic Process

Part of the diagnostic challenge for virus is sample may contain virus in the presence of various other cells, enzymes, and biological entities. The outer layers may be comprised of a lipid and protein wall and a protein envelope covering the nucleic acid. Other samples of interest also have outer layers including yeast, other fungi, bacteria and similar entities.

Steps Used in the Methods of the Present Invention
  Step 1. Provide a sample. In some embodiments the sample is provided in a vial. In some embodiments of the invention, the volume is measured and known. The sample can be saliva or a nasal swab. The sample may be other biological fluids. In some embodiments, the sample is provided by breathing into an apparatus. In some embodiments, the sample is provided by breathing onto a surface, collection media or filter.
  Step 2. Function A. Combine the sample with a water-miscible organic solvent and mix. In the technology of the method, the organic solvent releases the nucleic acid from the cell. The protein-containing envelope (if present) is removed from the RNA or DNA.

The sample may be added to the solvent or solvent may be added to the sample and mixed. In some embodiments, aprotic solvents such as acetonitrile, acetone, dimethyl sulfoxide (DMSO), tetrahydrofuran (THF), formamide dimethylformamide, formaldehyde, acetaldehyde, methyl ethyl ketone, ethyl acetate, N,N-dimethylformamide (DMF) or other aprotic solvents are used to release the viral nucleic acid. In some embodiments of the present invention, protic solvents such as methanol, ethanol, 1-propanol, 1-butanol, butyl alcohol or isopropyl alcohol, acetic acid, formic acid or other protic solvents may be added assist in the release the nucleic acids. The organic solvent added may be a mixture of one or more solvents. The organic solvent or solvents may contain water.

The organic solvent may contain a surfactant such as Tergitol 15-S-9, Triton X100 or other surfactants. The organic solvent may contain an ion pair reagent such as triethylammonium acetate (TEAA) or other ion pairing reagents. The following solvents may be used in the methods of the present invention: acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethylamine, ethylene glycol, formic acid, furfuryl alcohol, glycerol, methanol, methyl diethanolamine, methyl isocyanide, N-methyl-2-pyrrolidone, 1-propanol, 1,3-propanediol, 1,5-pentanediol, 2-propanol, propanoic acid, propylene glycol, pyridine, tetrahydrofuran and triethylene glycol.

In some embodiments of the present invention, the sample may be treated with hydrogen peroxide or other peroxide reagents before adding the solvent. Peroxide reagents can also be added at the same time as the solvent or after addition of the solvent. The peroxide may assist in lysis of the virus or other biological material. Peroxide in the sample may facilitate heating the sample at any step when contacted with a transition metal salt such as MnO, $Fe_2O_3$, CuO, $HfO_2$, $CeO_2$ and $Gd_2O_3$ and oxides of: Zr, Ti, Y, Fe, Cu, Ce, Gd, Hf and U.

In some samples, such as saliva, the process will precipitate at least some of the proteins and other biological material. Proteins may denature and may precipitate. In some embodiments of the invention, the concentration of the organic solvent after mixing is in the range of 0.5% to 50%, 1% to 95%, 5% to 70% or 10% to 60%. Control of the solvent concentration can be accomplished by controlling the relative volumes of the solvent and the sample. The solvent can be placed in a vial or container and sealed. A breath or liquid sample can then be added to the container. Using this method, the solvent concentration will be known.
  Step 2. Function B. RNase or DNase is deactivated or disabled in this step. This helps preserves the released RNA or DNA for detection, analysis, and quantification.
  Step 2. Function C. Proteins and biological materials are precipitated in the combined sample and water-miscible organic solvent mixture. The solids formed may increase by increasing the concentration of the organic solvent in the combined mixture. The solids may be dispersed in the sample by mixing.
  Step 3. Optionally, remove the particulate (i.e. precipitated) fraction present in the sample. In some embodiments of the present invention, the particulate is removed by centrifugation. In some embodiments of the invention, the particulate is removed by filtration. A filter may be fixed to a syringe for example and clarified material deposited into a vial. In some embodiments of the present invention, a syringe with a fixed needle may draw up clarified sample from a vial. The needle can preferentially draw up liquid and leave much, most, or all the solids in the vial. Then the syringe contents may be deposited without the solid fraction. In some embodiments, a plate filter or a centrifuge filter may be used to remove the solids.

Step 4. Optionally, add water to lower the concentration of the organic solvent. Polymerase enzymes may be deactivated by organic solvent through denaturation or precipitation. Dilution may be performed prior to amplification to prevent deactivation of polymerases by the solvent. However, in the methods of the present invention, some organic solvent will remain.

Step 5. Optional heating of the sample containing the water-miscible solvent. Heat may help increase the reaction rates of the solvent and additives.

Step 6. Add the amplification reagents including detection reagents to the treated sample and mix. Amplification and quantification may be performed by qRT-PCR in one example; however, any RNA or nucleic amplification and quantification method may be used. qPCR may be used to amplify DNA. Other nucleic acid amplification instruments may be used. In some embodiments of the present invention, the solvent of the invention may be included in the amplification reagents.

The nucleic acid that is released and stabilized sample may be added to the amplification reagents or amplification reagents may be added to the nucleic acid released and stabilized sample. In either case the concentration of the reagents is known and controlled. In some embodiments of the invention the organic solvent concentration in the sample prior to addition of the amplification reagents is reduced by a factor of >1, 1-2, 2-3, 3-4, 4-5, 5-10, 20, 30, 40 or 50. Reducing the concentration or organic solvent may preserve active polymerase or reactivate polymerase for amplification.

In some embodiments, the order of steps 1-5 may vary. In some embodiments of the present invention, the sample may be stored indefinitely after steps 1, 2, 3, 4, or 5 and then analyzed directly without purification of the nucleic acid. In some embodiments of the present invention, the stabilized sample may be purified by a silica or ion exchange column or magnetic bead process to recover the nucleic acid after steps 1, 2, 3, or 4 and then the sample may be amplified or detected and analyzed. In some embodiments of the present invention, a sample may be purified by a silica or ion exchange column or magnetic bead process to recover the nucleic acid. Subsequently, a water miscible organic solvent of the present invention can be added to the purified nucleic acid to stabilize and preserve the nucleic acid indefinitely. After nucleic acid stabilization and preservation, the sample may be amplified or detected and analyzed.

The sample is optionally diluted and then added to a master mix for RT-PCR or another amplification and detection method. Alternatively or additionally, a reagent can be added to the sample to render it suitable for amplification. The master mix can contain all the reagents necessary for amplification and quantification and in a further aspect, the present invention provides such master mix compositions. Optionally, the solvent of the present invention is present in the master mix. The concentration of the solvent of the present invention needs to be sufficient to lyse the cells. However, it is preferably not sufficiently too high to inhibit the enzymes reverse transcriptase, polymerase or any other essential enzyme that may be in the mixture. Also, the solvent must not inhibit the necessary annealing operations between the target nucleic acid sequence in the sample and amplification reagents such as primers. The lysing effect of the solvent may be enhanced with temperature; however, the deleterious effect of the solvent may be also enhanced with temperature. By way of example, concentrations of the solvent of the invention at the point at which the amplification reaction is carried out may be 0.5%, 0.6%, 0.7%, 0.8%, 0.9%, 1.0%, 1.1%, 1.5%, 2%, 3%, 4%, 5%, 6%, 7%, 8%, 9%, 10%, 11%, 15%, 20% or 25% (v/v), e.g. as a lower limit at which cell or virus lysis is possible but where the reagent used in the amplification reaction are active. The concentration may be higher provided the detection enzymes and primer annealing are not disrupted.

Manual Sampling and Parallel Processing of Sample

In some embodiments of the present invention, the sample may be identified with a barcode or other vial scanning identification. The identification will state the source of the sample and any other parameter associated with the sample. The instrument may be fitted with a barcode or another type of reader. With the scanning process, a light will show the slot in which the sample is inserted into the instrument. Any multi-parallel processing instrument may be used for analysis. In high throughput analysis, 96 well, 384 well or 1536 slotted instruments may be employed. The samples are processed in parallel, and any sample reporting positive results is matched with the information identifying the source and its parameters.

Any positive samples may be retested to confirm the presence of a virus or nucleic acid from a targeted cell. In this way, only negative personnel may be allowed to enter a plane, allowed into a country, allowed into a classroom, a playing field or any venue or location such as a company office or manufacturing plant. Because the sample is stabilized immediately, the integrity and fidelity of the result is higher than that of other methods. Because the solvent is completely stable and can be stored indefinitely, the integrity of the sampling process is higher than that obtained using other methods.

Quantification

High quality data requires that the RNA present in a sample is not degraded during the sampling process or at any time up until analysis and quantification. Degradation is not necessarily based on the time sampling and analysis, but may be caused by contaminants that vary from sample to sample such as RNase or DNase content, pH, other enzymes or by other means. Immediate stabilization of the nucleic acid from the biological entity and disabling RNase and DNase prevents degradation or other variables associated with the sample which can lead to false negative results.

Detection limit of analysis is the lowest number of nucleic acid molecules that can be detected within the sample. Since a specific number of viruses are associated with a specific number of nucleic acid molecules, this provides the threshold upon which a positive presence of the virus is indicated. The threshold is much lower and reliable if degradation of the nucleic acid is prevented upon sampling.

Reliable sampling also provides an indication of the progression of the disease or infection. Sampling done periodically and plotted on a timeline will indicate if the amount of virus is increasing or decreasing. In addition, because sample degradation is prevented, the absence of virus in the sample will reliably indicate a negative result. It is possible to determine whether the subject remains contagious or not, especially with repeated sampling and analysis.

Acquisition of the Virus Sample from the Biological Source

With stabilization of the nucleic acid, sampling can be performed at any location. This includes sampling at a point of care by medical personnel, laboratory personnel or alternatively, sampling can be performed at home. There are no restrictions, provided a kit and apparatus or fixtures are used to follow the process without error. Accordingly, the methods, devices and kits of the present invention represent a huge improvement over existing methods for virus detection in which sampling is performed solely by skilled personnel.

For example, a swab may be used to sample from the throat and/or nose using normal procedures. Or, virus can be obtained from a mouth swab, saliva or sputum. In some embodiments, a blood sample may be acquired by pricking or lancing a finger, taking the blood up in a capillary and depositing the blood into a container.

Sampling from urine feces, sputum and blood can be performed at home or in controlled setting with laboratory/medical personnel. Sampling from spinal fluid can be performed by skilled personnel and processed using the methods, devices and kits of the present invention.

In one example, a straw-type apparatus may be used to collect the aerosol from human breath. The straw may be equipped with a check valve so that only breath can be captured, and liquid cannot be drawn back into the mouth. The breath may bubble through the solvent of the present invention in an apparatus.

In some embodiments, the sample is placed in a sampling vial or tube or analysis vial or tube. In these embodiments, the sampling or analysis vial or tube can have an outside diameter of 9 mm or less, 4.5 mm or less, 2.25 mm or less.

The Effect of the Solvents of the Present Invention on Reverse Transcriptase and Polymerase Enzymes The solvents of the present invention are detrimental to proteins, lipids, and other cellular material while not harmful to nucleic acids. A positive effect of the detrimental property is the solvents disable or denature the enzymes RNase and DNase thus helping to preserve nucleic acids in the sample. However, this property is also harmful to two essential enzymes for amplification and detection of the nucleic acid. Reverse transcriptase is necessary to convert RNA into cDNA. It was discovered that for most reverse transcriptases, the maximum concentration of acetonitrile tolerated was 0.5% (v/v). Superscript II was found to tolerate 10% acetonitrile with only slight degradation of conversion of RNA to cDNA and Superscript III was found to tolerate 15-20% acetonitrile. Greater concentrations prevented the reverse transcriptase from converting RNA into cDNA. The other organic solvents of the invention behaved in a similar harmful manner.

Polymerase is necessary to amplify the DNA for real-time qPCR, end point detection qPCR and other methods. Taq or Pfu Polymerase was found to tolerate up to 10-15% acetonitrile. Bst Polymerase for LAMP was found to tolerate up 15-20% acetonitrile. Other organic solvents of the present invention behaved in a similar harmful manner.

Method, Devices and Kits for the Processing of Saliva, Sputum, Spit, Spittle Samples Saliva testing or Salivaomics is a diagnostic technique that involves laboratory analysis of saliva to identify markers of endocrine, immunologic, inflammatory, infectious, and other conditions. Saliva testing is used to screen for or diagnose numerous conditions and disease states. This type of testing typically involves collection of a small amount of saliva in a sterile tube followed by processing with a laboratory instrument. Proponents of saliva testing cite its ease of collection, safety, non-invasiveness, affordability, accuracy, and capacity to circumvent venipuncture as the primary advantages when compared to blood testing and other types of diagnostic testing.

Some methods of testing involve collecting saliva using a sorbent pad, applying a chemical solution, and monitoring for color change to indicate a positive or negative result. Virus detection by measurement of RNA usually requires processing a liquid and presenting a liquid to the measurement device and transducer. One method is to collect saliva by spitting or drooling.

Another method is collecting a passive drool. Passive drool (also called "mixed" saliva) can be used. Passive drool collection facilitates large sample volume collection. Since multiple samples can be readily obtained, saliva testing is particularly useful for performing chronobiological assessments that span hours, days, or weeks. This is quite important when testing for progression of a viral infection, or if the person no longer has detectable virus.

The passive drool collection method can be used to collect up to 1 mL or 2 mL of whole saliva without supervision. Acquiring larger samples may be performed especially if archiving samples after stabilization is desired.

In another example of the present invention, saliva from the column or magnetic bead method is deposited into a vial. In one embodiment of the method, the volume is adjusted to 1 mL. A 2.5 mL syringe containing 0.5 mL of a water-miscible solvent is used to pull the sample into the syringe. The syringe will contain 1.5 mL of liquid. The liquid is deposited into a vial and pulled repeatedly back into the syringe mixing the sample. The virus is lysed and stabilized ready for RNA detection and quantification.

In another embodiment of the present invention, 1 mL or more of drool/saliva is collected. A syringe containing 0.2 mL of an aprotic solvent is provided. A glass bead is provided in the liquid of the syringe. The bead may be irregularly shaped. The bead material may be plastic, polymer, metal, metal oxide or glass or anything that will travel through the syringe cavity and mix the solvents. A syringe containing 0.2 mL of DMSO is placed into the drool and 0.5 mL is pulled into the syringe. The syringe is designed so that the plunger movement is stopped when a defined amount of drool/saliva has been pulled into the syringe. The syringe is inverted several times allowing the bead to mix the solvent and sample. The stabilized sample is now ready for analysis however, the sample is stable and can be kept at room temperature or ambient temperature indefinitely.

Sampling an Individual or a Group

Sampling may be performed on an individual or a group of individuals. This ensures that no one individual has an active viral infection. Group sampling can be accomplished by sampling each individual within the group or by using pooled samples. Group sampling and analysis may be performed prior to permitting entry to any location including an airplane, school classroom, group event or a company site.

A barcoded or electronic coded sampling device such as a barcoded syringe would be matched to the identification of the individual or individuals. The identification would be entered into the detection instrument as the sample is loaded or when the sample is processed. Reporting of results would be matched to the identity of the sample and the individual. In these cases, the sampling and analysis is performed within 2 hours, preferably 1 hour, 30 minutes, 15 minutes or 5 minutes.

In some cases, an individual may be infected but may not yet produce detectable virus. It may be only a matter of hours before detectable virus is produced. In some embodiments, individuals may be retested in flight before landing. In this case, a sample can be obtained in flight using any sample type including sputum, spit or drool, nose swab or mouth swab. A barcoded or identification-coded sampling device can be matched to the individual. The sample is stabilized with the aprotic solvent of the invention. In some embodiments of the present invention, a protic solvent is used. The results could be determined while in flight, and entry into the airport or country can be informed by the results of the test. The stabilization devices, kits and methods of the present invention provide samples that are stable for 5 minutes, 10 minutes, 15 minutes, 30 minutes, 45 minutes, 1 hour, 2 hours, 4 hours, 8 hours, 12 hours, 1 day, 1 week, 1 month, 6 months, or indefinitely. Because RNA can be stabilized indefinitely using the method of the present invention, samples may be archived and analyzed at a later date or reanalyzed. A method for tracking and tracing analyzed samples and archived samples can be implemented because the samples are stable.

Contacting the Sample with a Reagent to Release the Viral Nucleic Acid

Place the swab into the lysis and stabilization solution and stir vigorously. Zika virus and COVID-19 are enveloped viruses. The outer envelope of the virus must be disrupted to release the nucleic acids from within the virus. The preferred releasing solution is the solvent of the present invention. However, the lysis solution may be a base or surfactant or any buffer or solvent capable of releasing RNA from a virus. The solvents of the present invention can immediately be added to the sample. The patient may be instructed to cough multiple times or more before a swab sample is collected. The sample may be obtained in a variety of ways including swabbing nostrils, cheeks, roof of mouth and/or under tongue.

A viral lysis reagent or solution removes the exterior proteins and exposes the nucleic acid of the virus. As the virus particles are lysed, RNA is released and is immediately vulnerable to RNase-mediated degradation. To prevent this, RNases that are present, and all proteins that are present, are immediately denatured or deactivated with a highly potent denaturing solvent, thereby stabilizing the released RNA. Inactivated enzymes include RNase and ribozymes.

A stabilization solution deactivates or denatures RNases that may be present in the sample, vial or reagents. In some embodiments of the invention, the deactivation agent is added at the same time as the lysis agent. The lysis agent and the deactivation agent can be the same reagent or mixture of reagents. In some embodiments of the invention, a reagent for lysis such as a surfactant and the reagent for denaturing or deactivating RNase is a water-miscible organic solvent. In some embodiments of the invention the lysis solution and the stabilization solution comprise a water-miscible organic solvent. In some embodiments of the invention(s) a water-miscible solvent can both lyse and stabilize the viral RNA sample.

Solvents include acetonitrile, DMSO, THF, DMF, acetone or other aprotic solvents. The requirement is that the solvent must be water-miscible and at a sufficient denaturing propensity or power and concentration to deactivate or denature the RNase protein invention. In some embodiments sufficient solvent is added to make the concentration 5% organic solvent (vol/vol). In some embodiments, the final concentration is 1-3%, 3%, 4%, 5%, 6%, 7%, 8%, 9%, 10%, 12%, 14%, 16%, 18%, 20%, 22%, 24%, 26%, 28%, 30%, 35%, 40%, 50%, 60%, 70% (v/v) or greater of the organic solvent. In some embodiments of the present invention, the solvent contains an ion pairing reagent such as triethylammonium acetate or a similar reagent. The reagent may contain a nonpolar cation to pair with the RNA and improve the solubility of the RNA. The solvent is lipid disrupting and protein disrupting while keeping nucleic acids soluble and intact.

Solvents inhibit nucleic acid amplification and may even facilitate error prone PCR. However, in the methods of the present invention, enough solvent is used to disable RNase and to optionally, remove the protein shell from the virus to expose the RNA or DNA. In some embodiments, the sample may be diluted with sterile RNase-free water or buffer prior to amplification.

FIG. 1 shows a syringe containing lysis/stabilization solvent and a mixer in one embodiment of the invention. Plunger 10 is inserted into a syringe barrel 20. The syringe contains solvent 30 and sample mixer 40. The end of the syringe has luer taper 50 onto which luer cap 60 may be inserted to seal the syringe and prevent solvent 30 from evaporating. Mixer 40 may be round or any shape and can be made from any material including plastic, metal, metal oxide or glass. Mixer 40 may be made of wire or a bead or beads. Mixer 40 may be shaped to prevent blockage of solvent 30 from exiting the syringe when plunger 10 is pushed downward. Alternatively, mixer 40 may be an air bubble.

Mixing may be performed with aspiration and dispensing of the mixture. A vortex or shaker can also be used for mixing. In some embodiments, the mixing is done in a chamber that can be placed in intimate contact with a swab or saliva sample or other biological sample and then may be subsequently sealed.

Figure 2:
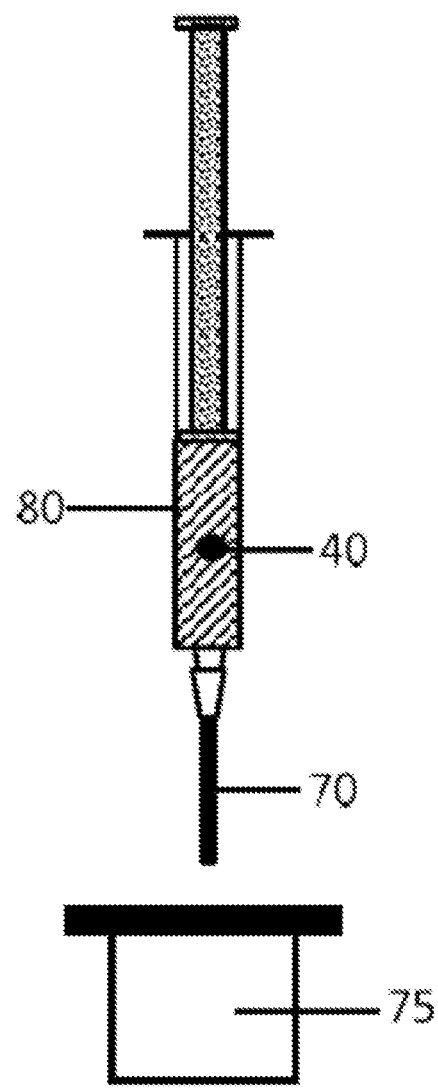
FIG. 2 shows a syringe containing a lysed and stabilized sample.

In FIG. 2, sample 75 containing possible virus or other materials of interest is pulled into the syringe via needle 70 and the syringe with sample and solvent is inverted several times to produce lysed and stabilized sample 80 which can be analyzed or stored. Mixer 40 travels through the syringe cavity mixing the sample and solvent. Sample 75 can be drawn into the syringe and mixed inside the syringe or mixed by repeatedly aspirating and dispensing solvent and sample. In other embodiments, the syringe may be used to dispense solvent used in the present invention into a sample.

In some embodiments, mixing is performed with one or more cycles of aspiration and dispensing of the syringe containing sample and solvent of the invention. In some embodiments, the mixture of sample and solvent of the invention forms a precipitate and a liquid.

The mixer may be used with any solvent including aprotic solvents provided the samples are aqueous-based and the solvents are water-miscible. In some embodiments of the present invention, a protic solvent is used.

In some cases, the diameter of the syringe used in accordance with the present invention is not greater than 9 mm. This includes the lip at the top of the syringe. Alternatively or additionally, in some cases, the syringe may be fitted into a liquid handler. In some embodiments of the present invention, the sample is placed in a vial, tube or reactor in the liquid handling instrument. In some embodiments of the present invention, the liquid handler may accommodate up to 96 samples in a 96-well format. In some embodiments of the invention, the diameter the syringe is not greater than 4.5 mm. In some embodiments of the invention the liquid handler may accommodate up to 384 samples. In some embodiments of the invention, the diameter the syringe is not greater than 2.25 mm. In some embodiments, the liquid handler may accommodate up to 1536 samples. In some cases, in particular where the sample containers are for manual use, larger diameters may be used.

The chemistry of the present invention is particularly suitable for use for breath sampling. In this embodiment, breath and a water-miscible organic solvent are combined. The solvent releases and extracts the RNA or DNA present in the sample and also denatures or deactivates RNase or DNase enzymes in the sample.

Figure 3:
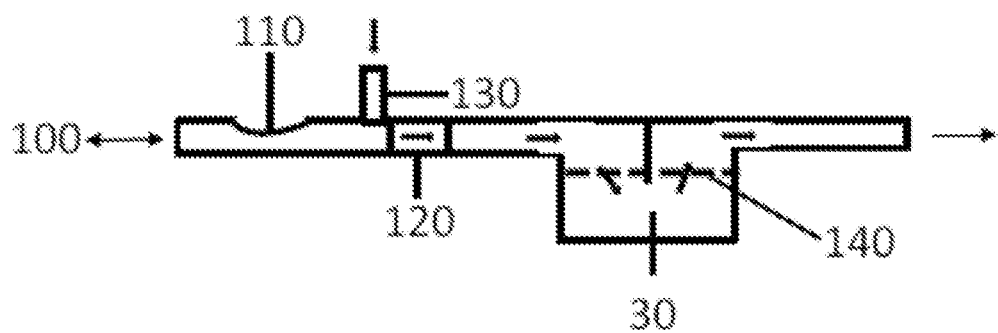
FIG. 3 depicts a device for direct lysis and stabilization of breath samples.

A device for direct lysis and stabilization of breath samples is shown in FIG. 3. Breath 100 is blown through a device containing solvent 30 of the present invention. The mouth is formed around the lip depression 110 to direct breath 100 through the device. Exhaled breath 100 contains liquid droplets formed from lining fluids that are held in the lung compartment and airway passages. These droplets contain numerous biomarkers including DNA, RNA, mRNA, proteins, metabolites, and volatile organic compounds. For patients infected with the flu or another virus, the droplets will contain viruses of interest. Typical condensate fluid yield expelled at normal tidal breathing effort is 75-150 microliters/minute for a child and 100-250 microliters/minute for an adult.

An exhaled breath collection device captures these droplets and presents them as sample in the solvent of the invention. A collection device may be used by an unsupervised patient in the home, workplace, laboratory, hospital, or clinic. This non-invasive handheld device is fully self-contained and disposable. As the subject breathes normally into the device, breath droplets can be collected in a cartridge. After collection the cartridge can be transported to another location for analysis. It can be transported by any means including the mail. This allows sampling anywhere including an airport, clinic, hospital, home, workplace, school, or any other reasonable environment. The droplets may be collected as a pool to be mixed into solvent of the present invention or may be collected directly into the solvent.

The device depicted in FIG. 3 contains inside one-way check valve 120 that directs breath 100 into the device but does not permit breath 100 to travel back out of the device. In some embodiments of the invention, outside one-way check valve 130 may also be positioned so that air may be drawn back into the individual but not through the device. Outside check valve 130 closes upon exhalation directing the breath droplets into the collection device. Breath 100 is directed through solvent 30 which can optionally contain a sorbent. Solvent barrier 140 prevents solvent 30 from reaching the open breath passage. The device may be disposable eliminating any cross-contamination.

Typical condensate fluid yield is 75-150 microliters/minute for a child and 100-250 microliters/minute for an adult at normal tidal breathing effort. One to two minutes of normal breathing can yield sufficient viral sample. In some embodiments, breathing can be continued for more than two minutes.

Figure 4A:
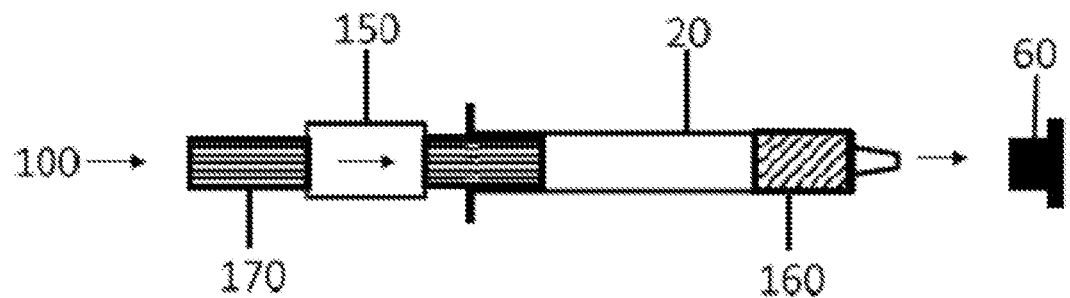
FIG. 4A shows a syringe comprised of a breath collection device.
Figure 4B:
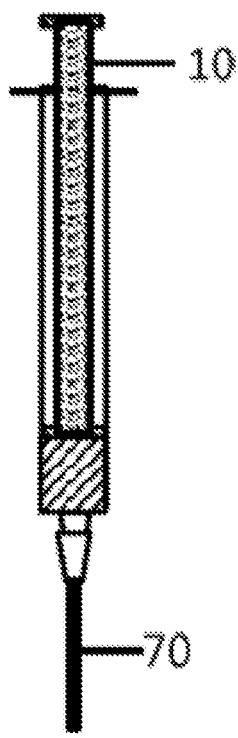
FIG. 4B is a depiction of the syringe shown in FIG. 4A after sample collection.
Figure 5A:
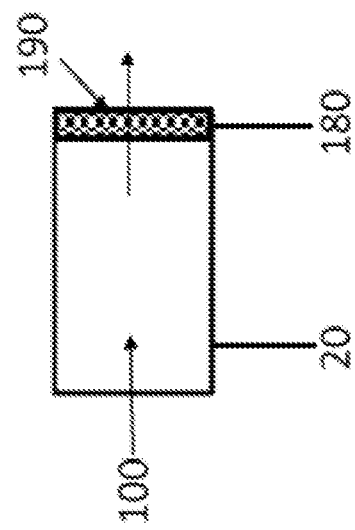
FIG. 5A is a depiction of a low backpressure syringe for breath collection.
Figure 5B:
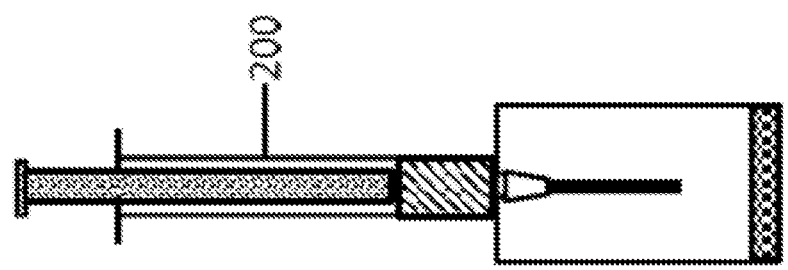
FIG. 5B shows a syringe dispensing solvent into the low backpressure syringe from 5A.
Figure 5C:
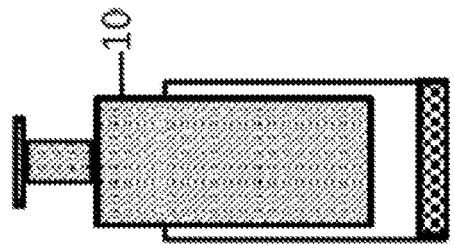
FIG. 5C depicts a syringe plunger positioned within the low backpressure syringe.

FIG. 4A shows a depiction of a breath collection device based on a syringe. A syringe fitted with a mouthpiece is used to collect the sample. Breath 100 from an individual is blown through mouthpiece 170 which contains one-way check valve 150 leading into syringe barrel 20. The individual can breathe into mouthpiece 170 for 5 seconds, 30 seconds, 1 minute, 2 minutes or more. One-way check valve 150 is used to allow breath, virus particles and other organic material to enter syringe barrel 20. One-way check valve 150 does not allow vapors from the solvent of the present invention to exit the syringe and be drawn back through mouthpiece 170 to an individual. Media with solvent 160 is contained in syringe barrel 20. Media with solvent 160 contains a support such as a sorbent paper material, glass wool or another material. Luer cap 60 is removed before breathing into the device. Luer cap 60 can be used to cap the syringe and the sample can be stored or shipped.

After the sample is collected, mouthpiece 170 is removed from syringe barrel 20 and syringe plunger 10 is inserted into the syringe as shown in FIG. 4B. The collected sample is in media with solvent 160. Syringe plunger 10 is used to manipulate various solvents to elute the prepared sample.

Additional solvent, reagents, water or buffer may be drawn up into the lysed and stabilized sample with syringe needle 70.

To remove the analyte, syringe needle 70 is placed on the end of the syringe and a solvent, water or buffer is drawn into the syringe and expelled a few times. Syringe plunger 10 may be depressed to expel virus (or another analyte) from media with solvent 160 through needle 70. The expelled solvent mixture is removed and analyzed.

In other embodiments, the solvent can be added after sample collection.

Although the sorbent pad/media is positioned within the solvent in FIG. 4A, it can be positioned anywhere along the syringe barrel.

In some embodiments of the present invention, water vapor is collected in the syringe or breath device of the invention. A sorbent pad, media or surface is not used but liquid droplets are collected and processed with the solvent.

In some embodiments of the present invention, the breath is expanded through an orifice to cool it so that droplets from breath condense and are collected.

A similar low backpressure syringe device is shown in FIG. 5. In FIG. 5A, the syringe bottom is open to reduce resistance to blowing through the device. Media 180 is contained in syringe barrel 20. The end of the syringe is removed and screen 190 is placed on the face of syringe barrel 20. Breath 100 is directed into the syringe. In this case, the device captures the breath vapor sample or liquid condensate and the solvent of the invention is added later.

In FIG. 5B, syringe containing solvent 200 is used to dispense solvent into syringe barrel 20 containing media 180.

In FIG. 5C, syringe plunger 10 is inserted into syringe barrel 20 to process the sample. As an alternative to the solvent addition method depicted in FIG. 5B, the solvent may be added with syringe plunger 10 to lyse and stabilize the sample.

The column media or collection media which can be comprised of paper, chromatography media or glass wool collects the air droplets containing virus, bacteria or other organic and biological samples. The collection media (paper, media, glass wool, etc.,) may be a strong or weak ion charger, affinity groups, hydrophobic or hydrophilic, adsorptive or non-adsorptive, porous, nonporous to facilitate capture. Droplets that contain the target virus, bacteria, etc. may be captured or organic molecules may be captured. Then, after the sample is collected, the solvent of the invention is added to lyse and stabilize the sample. Alternatively, the sample may be eluted directly using a solvent suitable for elution. In the embodiment shown in FIG. 5C, sample elution can be assisted by using a syringe plunger to draw up and dispense liquid for collection.

In some embodiments, the breath sampling method and apparatus with the solvent of the present invention may be used to sample for viral diseases including coronaviruses, COVID-19 and other diseases. In some embodiments, the breath sampling method and apparatus may be used to sample for viral pneumonia, influenza flu, other flus, bacteria, spores, chemicals and any biological material that is expelled from breath. In some embodiments, the breath sampling method and apparatus may be used to sample small organic molecules found in breath. A syringe breath device of the invention will not require solvent lysis for the collection of organic molecules.

Any device may be used that collects the aerosols or condensate from breath. FIGS. 6A and 6B are a depiction of the front and side views of a mask for virus collection. Mask 230 fitted with a filter device is used to collect virus, bacteria and chemicals as shown in FIG. 6A. Air is drawn through mask 230 and breath is directed through check valve 240 onto filter 250 as shown in FIG. 6B. A device of this type may be used for high sensitivity virus testing because the mask can be worn for an extended period of time.

Viruses present at low frequency can be detected. For example, the filter disc can be dropped in at the beginning of a shift, used for 5 minutes and then removed to test for virus. A device of this type may be used for patient who has trouble breathing such as a pneumonia patient or a COVID-19 patient.

Figure 7C:
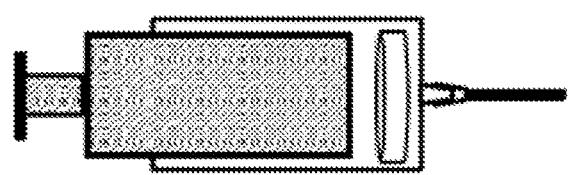
FIGS. 7A, 7B and 7C depict the processing of the filter recovered from the mask shown in FIGS. 6A and 6B.
Figure 7B:
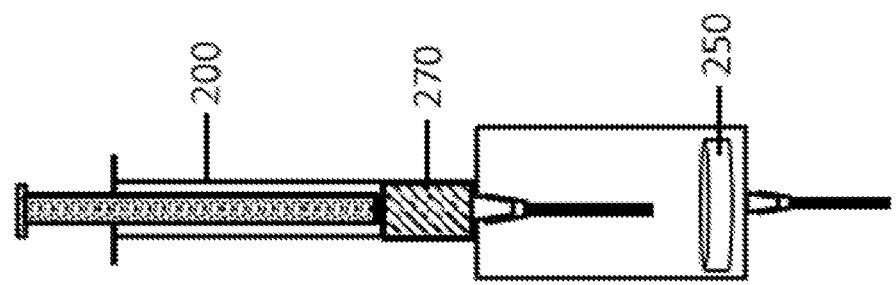
Figure 7A:
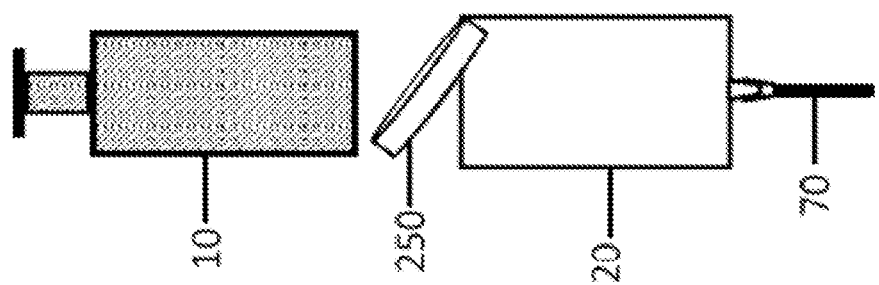

FIGS. 7A, 7B, 7C and 8 show how the filter may be recovered from mask 230 (shown in FIG. 6) and processed. Nucleic acid is eluted from filter 250 and processed. In FIG. 7A, filter 250 is removed from the mask and dropped into syringe barrel 20 fitted with needle 70. Syringe plunger 10 is removed.

In FIG. 7B, the filter is treated with solvent 270 using solvent adding syringe 260 to prepare the sample for detection.

Alternatively, plunger 10 is inserted into syringe barrel 20 to process filter 250 as shown in FIG. 7C. The syringe with filter 250 is used to aspirate the solvent of the invention through needle 70 and recover the sample from filter 250.

Or, in another embodiment, the filter may be added to the liquid of the invention in a container and the sample is transferred from the filter to the liquid.

Figure 8:
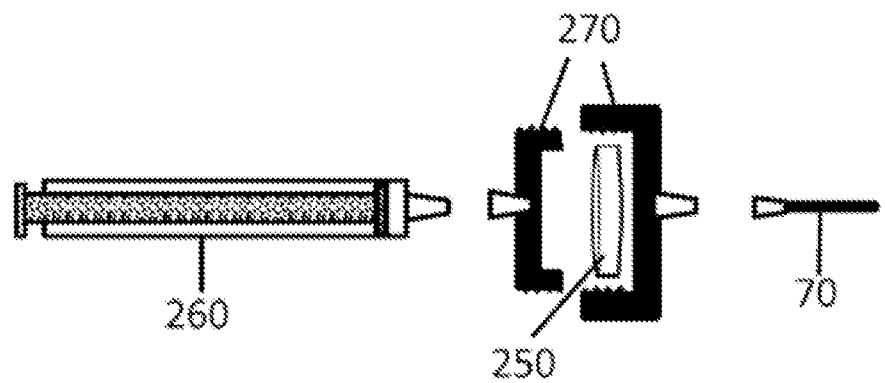
FIG. 8 shows the filter recovered from mask and processed with a syringe and filter holder.

In FIG. 8, filter 250 is recovered from a mask and processed with a syringe and a filter holder. The filter is added to filter holder 270 and syringe 260 and needle 70 are attached. The filter is treated with solvent of the invention to prepare the sample for detection. The solvent can be drawn in through needle 70, through filter 250 and into syringe 260. In some embodiments, the solvent can also be expelled through filter 250 and needle 70.

In some embodiments, the solvent of the present invention is not used and live virus or bacteria is collected. After collection, the sample may be processed using conventional nucleic acid sample preparation methods such as a column or magnetic bead purification or digestion with proteinase K. The nucleic acids can be processed normally with any reverse transcriptase method and amplification method for RNA and other amplification methods for DNA.

Figure 9B:
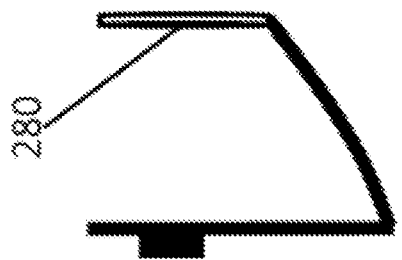
FIGS. 9A and 9B are a depiction of a half mask surface collection device for virus particles from breath.
Figure 9A:
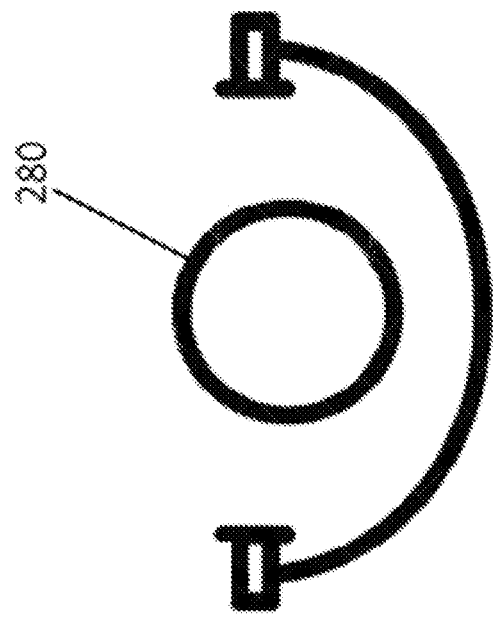

FIG. 9 shows a half mask device and surface designed to collect biological materials from breath. A front view is shown in FIG. 9A and a side view is shown in FIG. 9B. Collection surface 280 having a surface is used to collect breath containing virus particles or other biological material. In this example, collection surface 280 is contained in a mask with the surface directly in front of the mouth. Breathing and depositing vapor is performed on collection surface 280 that is ideally located in front of the patient's mouth, e.g., in a mask or shield. The mask can be worn for as long as needed to acquire the sample. This type of collection might be needed for children or people having trouble breathing or exhaling. Vapor droplets from the breath are deposited on the surface. In some embodiments, the collection surface may be on a platform or other structure on which breath vapor can be deposited.

The column, syringe or surface may be cooled with a piezoelectric device or other cooling method such as ice, etc. to enhance the collection of the breath droplets, for example using a Peltier device. The surface or device may be cooled in a refrigerator or similar device before use. It may be that the temperature is too high for vapor or breath condensate to collect, especially when warmed by the mouth. Droplets may not adhere, attach or condense depending on the temperature and dew point. A cool surface or tube will enhance or enable collection.

As described in the collection tube examples, the surface may be paper, plastic, glass, or metal that is porous or non-porous. The surface may contain collection wells or other structures to enhance collection. The surface may be hydrophilic or hydrophobic. The surface may contain ion exchange groups or any functional group or chemical group.

The surface or media may be polysulfone, Teflon, polyfluorinated or similar material, cellulose, cellulose nitrate, metal, polycarbonate, paper or paper material. Any material where droplets can accumulate can be used. The surface or media may have a smooth surface, a rough surface or a porous surface.

After collection, the surface is sampled with a swab or by rinsing with a solvent to collect the desired biological material for detection and analysis. Rinsing may be performed using the solvent of the present invention. Heating may be used to assist removal of frozen liquid.

After collection, the sample may be processed with conventional nucleic acid sample preparation methods including a column, magnetic bead purification or digestion with proteinase K. The sample nucleic acids are processed normally with any reverse transcriptase method and amplification method for RNA and other amplification methods for DNA.

After collection, the sample is lysed and stabilized with the solvent of the invention to detect the biological materials. In one, embodiment, a swab can be used to sample and process virus for detection and analysis. In another embodiment, a swab can be used to sample and process bacteria for detection and analysis.

Place Stabilized Nucleic Sample into a Shipping Container Tube, Vial, Syringe, Plate or Other Container A vial containing the sample can be placed into a package and mailed to a testing laboratory. The shipping may be accomplished with normal shipping temperatures. Dry ice or refrigeration, although acceptable, is not needed. In addition, the released viral nucleic sample remains stable so that analysis can be performed at will after receipt of sample at the laboratory with room temperature storage for days, weeks or months. Keeping a stable sample is accomplished by disabling or inactivating any RNase that may be present.

In some embodiments, the sample may be taken and analyzed at the point of enquiry. The sample is not shipped but rather the sample is taken and stored for a short duration such as a few minutes or a few hours and then analyzed. This is useful if the samples are taken, pooled and then analyzed together. However, for this procedure to be successful, the first sample taken must be as stable as the last sample taken. The stabilization device and method of the invention provides samples that are stable 1 hour, 2 hours, 4 hours, 8 hours, 12 hours, 1 day, 1 week, 1 month, 6 months, or indefinitely.

The virus, bacteria or yeast is disabled or non-infectious (and stable) upon addition or combination of the solvent of the present invention. This allows safe handling by non-trained personnel. The outside of the sampling apparatus, and shipping or containing envelope may be sprayed with bleach, alcohol or other disinfectants for additional safety. The envelope surface may be comprised of surfaces that facilitate disinfection. These surfaces include a thin layer of a monolayer of copper or silver for example.

Amplification and Analysis of the Viral Nucleic Acid

At the laboratory or instrument location, the sample stabilized with solvent can be diluted with buffer or deionized water. An internal standard, oligomer primers, a detection enzyme such as reverse transcriptase, polymerase, etc. added and RT, QPCR or LAMP is performed. In some embodiments, vials containing the stabilized sample are placed into a 96-well format rack and placed in the instrument or they may be placed directly into the instrument to detect the virus. Place into robot, defined aliquot removed and placed into 96 well plate or a 384-well plate or a 1536-well plate for analysis. The automation described for aprotic solvent sample analysis may also be used for other samples. In one embodiment of the invention a sample is taken manually, then analyzed 1-96 or 1-384 or 1-1536 at a time. This is accomplished by manually capturing the sample in a syringe or tube that can be placed in a 96-well or 384-well or a 1536-well format instrument. The sample that was captured manually is placed into the high throughput format and process with automation in parallel.

Complete Automation and Reporting

Testers may have to be certified and controlled. One or more negative results do not rule out the possibility of COVID-19 or other virus infection. Several factors could lead to a negative result in an infected individual, including poor quality of the specimen, containing little patient material. However, due to the method of the invention, a false negative will not occur from degradation of the sample.

In some embodiments, a positive control nucleic acid can be added at the point of lysis or at the point of analysis to ensure the amplification step is working properly. The positive control primers bind the control nucleic acid, but in the case of notifiable diseases such as COVID-19, the national disease control centers provide detailed guidance on primer sequences: https://www.cdc.gov/coronavirus/2019-ncov/lab/rt-per-panel-primer-probes.html A negative result indicates the lack of active virus present in the individual. However, a negative result may be the result of never having the virus, from collecting very late in the infection, or collecting very early in the infection. Nevertheless, an individual testing negative with the methods, kits and devices of the present invention indicates a low possibility or lower possibility of spreading the virus to other individuals.

In some cases, multiple samples may be collected and analyzed. For example, the progression of the disease may be determined.

If a negative result is obtained from a patient with COVID-19 symptoms or symptoms of another viral infection, particularly when only upper respiratory tract specimens were collected, additional specimens, including specimens from the lower respiratory tract should be collected and tested if possible. Each NAAT run should include positive and negative external controls as well as internal controls, and laboratories are encouraged to participate in external quality assessment schemes.

Kits, Formats and Kit Packaging

The present invention also provides kits for carrying out the methods of the present invention. Generally, such kits include a sample container for receiving the biological sample and a volume of a water-miscible organic solvent for combining the biological sample. The kits may further comprise one or more of a buffer for mixing with the biological sample, a cap for the sample container, nucleic acid amplification reagents to amplifying the target nucleic acid (e.g. a viral antigen) in the presence of the water-miscible organic solvent, reagents for detecting the target nucleic acid (e.g. a viral antigen) and/or a mail-in packaging for sending a collected and processed biological sample to a laboratory for testing.

Within a kit, the organic solvent may be formatted in different ways. The solvent may be contained in a syringe, pipette tip, dropper, vial (e.g. PCR vial or detection vial) or any manner where controlled amounts of solvent can be dispersed. The solvent may be contained with detection reagents, for example the enzymes and other reagents used in the amplification and/or detection reactions. The solvent may be in a larger stock container fitted with tools to dispense known, small amounts into samples or containers that will be used to hold samples. The solvent may be preloaded or prefilled in vials, syringes or other containers that can be combined with sample.

The volumes required may range 50 μL to 5 mL for a saliva sample or other samples that need stabilizing. For example, the sample can be quenched or stabilized with a semi-automatic sampler which could be set at a fixed volume and utilize push dispensing.

The solvent can be contained in a capsule or pillow. The capsule can be opened with piercing or another mechanism.

For kits for use at-home use, their design is important and should take account of some or all of the following points. The solvent in the kit need to be stable for years. Generally, the solvent is stable after addition to the sample and up until analysis. For at-home sampling, the kits of the present invention are preferably fool proof, in operation and the sample container processed according to the methods described herein is capable of being mailed in to the processing laboratory. Additionally, it is preferable that the processing of the kit is relatively easy and inexpensive, for example by processing the results is an automated manner that minimizes the occurrence of false positives and negatives. It is also preferred that the kits have a reasonable and practicable shelf life, for example enabling at-home kits can be kept at home until an emergency, allowing kits can be purchased in advance and stored in a cabinet or cupboard. In general, the kits can also be used for group analysis.

EXAMPLES

Diagnostics is a large application of the technology of the invention. However, besides diagnostics, the technology may be used for any R&D application. For example, samples may be taken and treated for RNA sequencing to determine mutations. In this case, samples may be used to make a cDNA library and then sequenced by Illumina and nanopore and other technologies. One variant of COVID-19 in the United Kingdom had 23 mutations 2-4 months into the COVID-19 pandemic. The number of mutations rapidly became much higher, and it was desired to track these mutations.

Example 1. Capturing Nucleic Acid from Virus Particles Associated with High-Risk Infectious Diseases A method of storing a virus sample is described in which a biological sample is placed into a vial, tube or container and an aprotic solvent is combined with the sample to release and extract RNA present in the sample. The solvent denatures or inactivates any RNase present in the sample. The process may be used at group events, schools, companies, churches or any place with a group of people gather in close contact for a limited time. The method is useful in situations prior to boarding a plane, entering a classroom or entering a workplace. For example, prospective airline passengers may have samples taken at the airport or gate and analyzed prior to boarding. No one having active viral infection would be allowed to board the plane. In this way, all passengers and crewmembers can be assured of safety during the flight. This use of the method may be useful for passing through point of entry at the flight destination as well.

The success of the method is due to the ability to immediately stabilize the sample at the point the sample is taken. Stabilization can be performed within 1 minute of taking the sample within 2, 3, 4, 5, 6, 7, 8, 9 or within 10 minutes of taking the sample from an individual. Rapid stabilization ensures a false negative is not received due to sample instability.

Example 2. Eliminating the Risk of Viral Infection and Simultaneously Enhancing the Capture and Stabilization of RNA During Detection Hydrogen peroxide heat and removal. A saliva (or swab, breath, etc.) sample with suspected COVID-19 is mixed with an equal volume of acetonitrile (final concentration, 50% vol/vol) and 1% hydrogen peroxide (final concentration 0.5% vol/vol). The virus is immediately neutralized, and the virus particle collapses to release lipid, capsid proteins and genomic RNA.

In some examples, detection is preceded by a heating step to improve sensitivity and specificity in RNA detection. In some examples, hydrogen peroxide is diluted prior to detection. In some examples, acetonitrile is diluted prior to detection.

To heat the sample and to eliminate hydrogen peroxide, the sample is combined with a transition metal catalyst such as $MnO_2$, which safely decomposes hydrogen peroxide (which can be present in VTM) yielding water and oxygen in a highly exothermic reaction. Heat may further inactivate RNase. A transition metal oxide or a similar catalyst may be used. For example, $MnO_2$ or $KMnO_4$ or any similar transition metal salts may be used. The metal oxide can be immobilized or impregnated/shielded by a membrane or a surface coating.

The viral RNA or DNA is now ready for assay by RT-PCR, LAMP or some other amplification technique. The sample can now be used in any downstream assay (RT-PCR, RT LAMP, qPCR, PCR, etc.) or assay test.

The introduction of simple transition metal catalysis to eliminate the excess hydrogen peroxide is highly exothermic and promotes RNase inactivation, while maintaining RNA integrity.

Example 3. Lysis and Stabilization of RNA from Yeast

A colony PCR was performed on yeast colonies plated on YPD. Plates of *Saccharomyces cerevisiae*, strain 518 (gdp::) was used in the experiments. Other strains were used including Baker's Yeast available as a pure culture from Amazon.

From an agar plate, several small samples of a yeast colony (approximating to 10% of a pinhead-size colony) were picked with a p200 pipette tip and resuspended in 30 μL solvent. $ddH_2O$, 50% v/v acetonitrile/100 mM TEAA and 0.2% Sodium dodecyl sulfate in DI $H_2O$ were used as the solvents to resuspend the yeast colony. Replicates of each solvent resuspension were made, and one of each replicate was heated at 99° C. for 5 minutes. 1 μL from each suspension was added as DNA template in a 25 μL PCR experiment.

Various primers were used in the PCR experiment. Primer stocks were purchased from Eurofins genomics, diluted to 5 mM, and a final concentration of 0.4 μM was used in the 25 μL PCR. Additionally, 2.5 μL 10× Taq Mg-free reaction buffer (NEB), 1 μL 25 μM $MgCl_2$ (NEB), 2 μL 1.25 mM dNTP mix (NEB), and 1 μL polymerase (extracted in lab) were added to the PCR, which was then made up to 25 μL by with $ddH_2O$.

The PCR was carried out using a standard OneTaq PCR protocol: samples were heated at 95° C. for 30 seconds, prior to 40 cycles of 94° C. for 30 s, 58° C. for 30 s, and 68° C. for 60 s, before finishing with 68° C. for 5 minutes to ensure all amplicons had been fully extended. 10 III PCR amplicons were then loaded onto a 1% agarose gel, which was run at 85V for 40 minutes. Bands were visualized in a G:Box gel imager.

The results of this PCR experiment show that acetonitrile released the DNA from the yeast.

Acetonitrile at a final concentration of 2% up to 20% did not impede the ability of the PCR to amplify specific DNA products. The PCR amplicons containing acetonitrile gave similar band intensities to those containing only $ddH_2O$.

Example 4. Lysis and Stabilization of RNA from Bovine Liver

Liver was purchased from the local market. A 2-gram portion was mixed by grinding with 2 mL 50/50% (v/v) acetonitrile. The supernatant was isolated and diluted 3-fold. PCR was carried out as in Example 3. The results showed that RNA was released and amplified.

Example 5. Procedure for Sample Prep and Direct Detection of Virus in Saliva, Nostril Swab and Other Biological Samples Acetonitrile Lysis and Preservative Solution:
1. An acetonitrile solution is formulated to contain pH 5.6 sodium citrate.
2. Prepare a citrate stock solution of 50 mL 1M sodium citrate from disodium citrate (254.1 g/mole). Into a 40 mL flask, add 12.7 g to 40 mL DI water and dissolve crystals.
3. Add glacial acetic acid drop-wise to obtain a pH of 5.6±0.2. Citrate has three ionizable carboxylates. The initial solution will have a pH above 8. The pH will come down quickly at first and then more slowly around pH 6.5 as the acid is added.
4. Quantitatively transfer to a 50 mL volumetric flask and make up the solution to a final volume of 50 mL.
5. Filter sterilize into a Falcon tube (or similar storage tube.)
6. To a 50 mL volumetric flask, add 40 mL of acetonitrile. Add 1 mL of the pH 5.6 sodium citrate buffer and mix. Add acetonitrile to volume and mix. The final solution contains 20 mM sodium citrate.

Procedure:
1. Transfer (for example, 25 μL) of a saliva or swab sample to a clean microfuge tube and add an equal volume of the acetonitrile preservation solution. The sample optionally contains viral transfer media (VTM). Vortex mix. This extract will contain soluble viral RNA and cellular material.
2. Optionally, heat to 90° C. in a thermal cycler for 4 min.
3. Optionally, centrifuge the extract for 2 to 5 min on a bench-top microfuge to pellet any insoluble material.
4. Prepare RT-PCR master mix and pipette 10 μL into PCR vial.

5. Pipette the sample to PCR vial. There should be no transfer of precipitated material. For a 20 µL PCR vial, add 6 µL of sample and 4 µL of DI water. This may be adjusted depending on master mix amounts, acetonitrile concentration and procedure. Vortex mix.
6. Place in instrument, amplify and detect via RT-PCR.

Notes:
1. Saliva may be analyzed directly with this procedure. Saliva samples preserved in VTM may be lysed and preserved in the acetonitrile/citrate solution and then analyzed. VTM should not contain any buffer that has a higher buffering capacity of the acetonitrile/citrate solution or will raise the pH of the sample when mixed with acetonitrile/citrate.
2. Swab sample in DI water may be analyzed directly with this procedure. Saliva samples preserved in VTM may be lysed and preserved in the acetonitrile/citrate solution and then analyzed. VTM should not contain any buffer that has a higher buffering capacity than the acetonitrile/citrate solution or will raise the pH of the sample when mixed with acetonitrile/citrate solution.

Example 6. COVID-19 Testing with Ribostay Using Nasopharyngeal Swab and Saliva Samples Ribostay formulation: (40% acetonitrile (v/v), 20 mM sodium citrate, pH5.6, 1% hydrogen peroxide (v/v)). Ribostay was used to dilute all samples 1:1, reducing all final concentrations by 2-fold. Where a sample is presented in a solid form, add Ribostay directly at a 2-fold dilution. In a typical RT-PCR procedure:
1. Add 25 µL Ribostay to 25 µL of a liquid clinical sample.
2. Vortex for 15 seconds and then heat at 90° C. for 4 min.
3. Vortex again and withdraw 5 µL for RT-PCR.
4. Dilute the 5 µL sample with 45 µL nuclease-free water.
5. Add 5 µL of diluted sample to a 20 µL (final volume) RT-PCR reaction.
6. Amplify between 25-40 cycles as per the COVID-19 kit instructions (Chai Biotechnologies).

For many RT-PCR kits, it is important to ensure the final concentrations of Ribostay components are less than: 0.5% acetonitrile, 0.5 mM citrate and 0.025% peroxide in the final assay. An experiment to measure the tolerance of reverse transcriptase to the solvent of the invention tolerance was performed. Superscript II and NEB MMLV were found to tolerate acetonitrile concentrations of at least 10% (v/v).

Example 7. Isolation of Total RNA from Cells: Protocol for RNA Extraction from Yeast 1. Lyophilized yeast cells were mechanically disrupted by hand grinding for one minute using standard procedures.
2. 500 mg (approximately) of ground material was transferred to an Eppendorf tube.
3. 1 mL of Ribostay was added and mixed thoroughly.
4. The mixture was centrifuged (bench top 15000 rpm, 5 minutes)
5. The supernatant was removed and 10-20 µL underwent electrophoresis on a 1% agarose gel.
6. RNA was identified by the characteristic appearance of ribosomal and transfer RNA species using a fluorescence dye. Ethidium bromide or "Gel Green" were used via a suitable transilluminator.

The complete process took 1 hour from start to finish. Samples were analyzed directly or were concentrated by standard ethanol precipitation, 10 minutes at room temperature. The precipitate was collected by a 5 min bench centrifugation at 15000 for 5 minutes. The supernatant was discarded, and excess ethanol removed. The sample was dissolved in 500 µL Ribostay.

Example 8. Modelling Isolation of RNA from Mammalian Enveloped Viruses Using Bacterial Enveloped Double Stranded RNA Bacteriophage phi6

Bacteriophage phi6 is a restricted host range phage that infects Pseudomonads including the plant pathogen *Pseudomonas syringae*. Infection and lytic growth were achieved as follows: Plate *P. syringae* on TSB plates (the recommendations are as per the manufacturer) and culture in the same broth. Inoculate a broth culture (use 2.5- or 25-mL volumes in Sterilin or Falcon tubes). Do not exceed 30° C. (use room temperature: approx. 24° C.) with either a single colony or 50-100 µL overnight broth growth.

Incubate with gentle shaking, but good aeration, for 2-5 hours, before adding the phage (typically 200 phage particles per mL culture).

Incubate for at least 8 hours (or overnight). The outcome was weak bacterial growth, compared with an uninfected culture that had significant growth. This showed that the viral infection was productive/effective.

Harvest the supernatant and discard the cell debris. (Centrifugation or use a syringe with 0.22 µm filter).

Materials and Reagents:
TBS (1×) or Tris Buffered Saline: 50 mM Tris-HCl pH 7.5, 150 mM NaCl, filter or autoclave for sterility. PEG/NaCl (5×) stock solution: PEG-8000 20%, NaCl 2.5 M. Dissolve 100 g PEG-8000 (20% w/v) and 75 g NaCl (2.5 M) in 400 ml ddH2O and bring to a final volume of 500 mL by stirring at room temperature. Sterilize with a 0.2 µM filter.

Procedure:
1. 1500 µL of bacterial culture containing the phage particles was transferred to a microfuge tube.
2. The bacteria were separated by microcentrifugation for 2 min at 13,000×g.
3. 1200 µL of supernatant was transferred to a clean microfuge tube taking care of not touching the pellet of bacteria with the tip.
4. 300 µL of PEG/NaCl 5× was added and mixed thoroughly by inversion; do not vortex.
5. The tube was chilled on ice. After a few minutes, the tube was removed and wiped clean with a clean tissue to expose the supernatant to indirect lighting. By rocking the tube back and forth with the fingers, PEG-precipitated virions are often seen to the naked eye. If a precipitate is visible, the incubation can be shortened to 5 min, otherwise continue the incubation on ice for up to a full hour.
6. The virions were pelleted by microcentrifugation for 3 min at 13,000×g.
7. The bulk of supernatant was carefully removed with a large tip and discarded in an appropriate container, taking care to prevent spreading bacteriophage on gloves and pipettors. The solution was micro centrifuged again for 1 min at 13,000×g; all residual supernatant was removed with a 100 µL tip and the tip discarded. The second centrifugation is essential to 1) collect all the phage particles at the bottom of the tube and 2) achieve a complete removal of bacterial supernatant.
8. The pellet was resuspended by vigorous vortexing with 120 µL of TBS (1×) (1/10th of the initial culture volume)

and incubated on ice for another hour. Sometimes, it is easier to let the pellet soften for a few min before resuspending the virions. The incubation time can be shortened when large amounts of virions are precipitated but a safe 30 min incubation step is recommended to prevent a loss of particles during the clearing step.

9. The mixture was vortexed vigorously again and cleared the phage solution by microcentrifugation for 1 min at 13,000×g. The phage solution was transferred to a clean microtube and virion was quantified.

10. The particles were stored by refrigeration.

RNA isolation from phage: phi6 mimics influenza-like viruses including COVID-19. It is an enveloped phage with proteins inserted as spikes in a lipid bilayer (this is known from EM structures). Ribostay was shown to be sufficient to inactivate the phage and release the RNA. 50 µL Ribostay was added (formulation as above without peroxide [20% ACN/10 mM citrate, pH5.6]) to an equal volume of phage particles (unknown titer). This was mixed 20 seconds with a pipette. A series of sample volumes were loaded onto an agarose gel. The results: Ribostay striped the envelope, released the RNA and stabilized the RNA. The RNAs that were released are double stranded and were used as clean templates for RT-PCR/LAMP trials.

The addition of (final conc) 10 mM sodium citrate (at pH 5.6) enhanced extraction and gave good stability for RNA. There is often a heat step used either prior to PCR or as part of the processing of samples. It was established that the addition of 0.5% hydrogen peroxide had little effect on extraction yields but may offer protection against RNase degradation at 90° C., a heat step that is often employed.

Example 9. Acetonitrile Inactivation of COVID-19 Virus

In one set of experiments, live COVID-19 virus was mixed with acetonitrile to a final concentration of 50% v/v. The solutions, with and without acetonitrile, were added to SARS-CoV-2 seed stock before incubating with VERO E6 cells. Incubation was for 48 hours at 37° C. Successfully infected cells were measured using spike protein staining after 48 hours of incubation. The results showed that without the acetonitrile, the infection rates were at 90%. With acetonitrile, the infection rates were zero and equivalent to uninfected cells. The experiment was repeated four times with the same results. These results show that contact between COVID-19 virus or other virus and the water miscible solvents of the present invention results in inactivation of the virus and allows the safe processing of biological samples according to the methods described herein.

The invention claimed is:

1. A method for detecting a target nucleic acid in a biological sample, comprising:
   (a) mixing an unprocessed biological sample containing virus or cells with a water-miscible organic solvent alone, whereby the virus or cells present in the unprocessed biological sample are lysed to release nucleic acid, thereby providing a processed biological sample;
   (b) combining the processed biological sample with nucleic acid amplification reagents alone, to provide a diluted biological sample;
   (c) amplifying the target nucleic acid in the presence of the water-miscible organic solvent to provide an amplified sample, wherein the concentration of the water-miscible organic solvent is 0.5% to 20% (v/v); and
   (d) analyzing the amplified sample to detect the presence of the target nucleic acid.

2. The method of claim 1, wherein the water-miscible organic solvent is selected from the group consisting of acetonitrile, DMSO, THF, DMF, acetone, and formamide, or a combination thereof.

3. The method of claim 2, wherein the water-miscible organic solvent is acetonitrile and the nucleic acids are viral or cellular RNA or DNA.

4. The method of claim 1, wherein the biological sample is selected from the group consisting of a biological fluid, blood, urine, stool (feces), tissue, organ tissue, spinal fluid, nasal material, sputum, breath and saliva.

5. The method of claim 4, wherein the biological sample is present in the breath of a subject and wherein the biological sample is captured by breathing into a sample container or onto a surface held in front of the mouth of the subject.

6. The method of claim 5, wherein the biological sample is comprised of breath, wherein the breath contains liquid, and wherein the liquid is captured on sorbent, media or surface associated with the sample container.

7. The method of claim 1, wherein breath is captured with a device comprising a chamber having an inlet and an outlet for breath, the chamber having a surface, sorbent or media onto which breath particles collect and means to recover the liquid particles from the surface, sorbent or media by scraping, swabbing, dripping or rinsing with a liquid.

8. The method of claim 7, wherein the surface, sorbent or media is cooled.

9. The method of claim 1, wherein following step (a), the nucleic acids in the water-miscible organic solvent are separated from the solid components of the biological sample.

10. The method of claim 1, wherein the virus in the biological sample is selected from the group consisting of Severe Acute Respiratory Syndrome Coronavirus-2 (SARS-CoV-2), Human Immunodeficiency Virus (HIV), measles, Herpes simplex, varicella-zoster virus (VZV), Respiratory syncytial virus (RSV), Epstein-Barr virus, Cytomegalovirus (CMV), Coronaviruses, Rotavirus, Hepatitis, human papillomavirus (HPV), Influenza (flu) and BK virus.

11. The method of claim 1, wherein following step (a), the processed biological sample is heated, stored or transported.

12. The method of claim 1, wherein following step (a), the processed biological sample is stored for at least 3 days at ambient temperature between about 15° C. and about 30° C.

13. The method of claim 1, wherein steps (a) and (b) are performed simultaneously.

14. The method of claim 1, wherein step (a) occurs prior to step (c), and wherein the processed biological sample is diluted with water or buffer between steps (a) and (c).

15. The method of claim 13, wherein the water-miscible organic solvent is present at a concentration of 0.5% v/v in the diluted biological sample.

16. The method of claim 1, wherein step (c) includes reverse transcriptase and another polymerase.

17. The method of claim 1, wherein step (d) is performed using RT-PCR, PCR, qPCR, LAMP or EXP AR.

18. The method of claim 1, wherein the cells are bacterial.

19. The method of claim 1, wherein the analyzing step (d) is carried out using an antibody specific for the target nucleic acid or a nucleic probe specific for the target nucleic acid.

20. The method of claim 1, wherein the method results in preservation of the target nucleic acid.

* * * * *